United States Patent [19]

Henderson et al.

[11] 4,012,306

[45] Mar. 15, 1977

[54] PRODUCTION OF HIGHLY SOLUBLE, SOLID, RESINOUS, HIGHLY CHLORINATED ALPHA-OLEFINIC HYDROCARBON MATERIAL

[75] Inventors: Albert J. Henderson, Coraopolis; John E. Krol, Moon Township, both of Pa.

[73] Assignee: Neville Chemical Company, Pittsburgh, Pa.

[22] Filed: Oct. 7, 1974

[21] Appl. No.: 512,908

Related U.S. Application Data

[63] Continuation-in-part of Ser. No. 449,756, March 11, 1974, Pat. No. 3,896,183, which is a continuation-in-part of Ser. No. 267,444, June 29, 1972, abandoned.

[52] U.S. Cl. .......................... 204/163 R; 260/660; 526/43

[51] Int. Cl.² ...................... B01J 1/10; C07C 17/06

[58] Field of Search ................. 260/660; 204/163 R

[56] References Cited

UNITED STATES PATENTS

| | | | |
|---|---|---|---|
| 3,330,877 | 7/1967 | Kircher et al. | 260/660 |
| 3,896,183 | 7/1975 | Henderson et al. | 204/163 R |

*Primary Examiner*—Leland A. Sebastian
*Attorney, Agent, or Firm*—Burns, Doane, Swecker & Mathis

[57] ABSTRACT

Highly soluble solid resinous highly chlorinated alpha-olefinic hydrocarbon material contains above about 65% chlorine, has a ring and ball softening point of above about 90° C, and is completely soluble and gel-free initially and after 24 hours in xylene (50% solution).

19 Claims, No Drawings

PRODUCTION OF HIGHLY SOLUBLE, SOLID, RESINOUS, HIGHLY CHLORINATED ALPHA-OLEFINIC HYDROCARBON MATERIAL

CROSS REFERENCE TO RELATED APPLICATIONS

This is a continuation-in-part of our commonly assigned U.S. patent application Ser. No. 449,756, filed Mar. 11, 1974, now U.S. Pat. No. 3,896,183 which in turn is a continuation-in-part of commonly assigned U.S. patent application Ser. No. 267,444, filed June 29, 1972, now abandoned.

BACKGROUND OF THE INVENTION

Waxes and resinous wax derivatives have attained an important position as industrial raw materials. The characteristics of these materials include, for example, resistance to water and water vapor, tensile strength, ductility, gloss, hardness, ability to emulsify, solvent retention, moldability and melting range. One group of wax derivatives comprises the chlorinated hydrocarbons, e.g., chlorinated paraffins. Chlorinated paraffins may be liquid, semi-fluid, or solid, depending on the type of paraffin and degree of chlorination. The chlorine content of known grades is in the 30% to 70% range, the solid containing about 70% chlorine. See, for example, U.S. Pat. No. 3,567,610. The higher chlorinated paraffins are generally soluble in chlorinated solvents, esters, ketones, aromatic hydrocarbons and terpene solvents. However, some of the highly chlorinated e.g., 70% chlorinated, paraffin materials when mixed in these solvents have been found to leave a small quantity, e.g., less than 1%, of an insoluble residue or gel dispersed in the solution.

This partial insolubility of highly chlorinated paraffinic wax has been a problem area for the paint formulator who desires crystal clear, completely soluble chlorinated material. (Paints and other protective coatings constitute a major use for highly chlorinated hydrocarbon wax.) In the past, efforts to solve this partial insolubility of the highly chlorinated hydrocarbon material have resulted in undesirably lower softening points, i.e., below about 90° C (ring and ball) and/or an undesirably lower chlorine content, e.g., below about 65% chlorine. One laborious technique which has been utilized in an attempt to solve this partial insolubility involves selective precipitation and filtration to remove the insoluble matter.

SUMMARY OF THE INVENTION

Accordingly, a primary object of the present invention is to produce a highly soluble, solid, resinous, highly chlorinated hydrocarbon material which does not possess or incur, or which substantially alleviates, the problems of the prior art as discussed above.

A more specific object of the present invention is to produce a novel, solid, resinous chlorinated hydrocarbon material which contains above about 65% chlorine, has a ring and ball softening point of above about 90° C, and is completely soluble and gel-free initially and after 24 hours in aromatic hydrocarbon solvents such as xylene.

Other objects of the present invention include providing novel processes for producing these highly soluble solid resinous highly chlorinated hydrocarbon materials, and novel solutions containing such highly chlorinated hydrocarbon material.

In accordance with one aspect of the present invention, a solid resinous chlorinated alpha-olefinic hydrocarbon material is produced, which chlorinated alpha-olefinic hydrocarbon material contains above about 65% chlorine; has a ring and ball softening point of above about 90° C; and is completely soluble and gel-free initially and after 24 hours in aromatic hydrocarbon solvents such as xylene (50% solution −25° C.)

In accordance with another aspect of the present invention, a solid resinous chlorinated alpha-olefinic hydrocarbon material is produced which consists essentially of a mixture of chlorinated alpha-olefinic hydrocarbons having an average of above about 26 carbon atoms per hydrocarbon molecule, the chlorinated alpha-olefinic hydrocarbon selected from the group consisting of hydrocarbons containing from about 20 to about 35 carbon atoms, and which chlorinated alpha-olefinic hydrocarbon material contains above about 65% chlorine, has a ring and ball softening point of above about 90° C, and is completely soluble and gel-free initially and after 24 hours in aromatic hydrocarbon solvents such as xylene (50% solution −25° C.)

In another more specific and preferred aspect of the present invention, a solid resinous chlorinated alpha-olefinic hydrocarbon material is produced, which chlorinated alpha-olefinic hydrocarbon material consists essentially of a mixture of $C_{24}$ to $C_{28}$ chlorinated alpha-olefinic hydrocarbons, the mixture having an average carbon number of above about 26, and the chlorinated alpha-olefinic hydrocarbon material having a chlorine content of between 68% and about 70%, a ring and ball softening point of between about 90° C and about 95° C, a color (Gardner scale — 15 grams/100 ml $CCl_4$) of less than about 1.5; a heat stability value (JQD) between about 0.1 and 0.3; a specific gravity at 25° C of between about 1.60 and 1.65; and which is completely soluble and gel-free initially and after 24 hours in aromatic hydrocarbon solvents such as xylene (50% solution −25° C.)

In accordance with another aspect of the present invention, processes are provided for producing such solid resinous chlorinated hydrocarbon materials, which processes include chlorinating an alpha-olefinic hydrocarbon material to produce a chlorinated alpha-olefinic hydrocarbon material containing above about 65% chlorine, having a ring and ball softening point of above about 90° C, and being completely soluble and gel-free initially and after 24 hours in aromatic hydrocarbon solvents such as xylene (50% solution −25° C.)

In another aspect of the present invention, aromatic hydrocarbon solutions of highly chlorinated hydrocarbon materials are provided, which solutions contain a chlorinated alpha-olefinic hydrocarbon material having a chlorine content of above about 65%, a ring and ball softening point of above about 90° C, and which solutions are clear and completely gel-free.

These and other objects, aspects, and advantages of the present invention will be apparent to those skilled in the art from the following description of the preferred embodiments and the appended claims:

DESCRIPTION OF THE PREFERRED EMBODIMENTS

The alpha-olefinic hydrocarbon material which is chlorinated in accordance with the present invention may be natural or synthetic in origin and is a solid at ambient condition, i.e., 25° C and 760 mm Hg. The more preferred alpha-olefinic hydrocarbon mixtures typically contain alpha-olefinic hydrocarbons having from about 20 to about 35 carbon atoms. The mixtures also preferably have an average carbon number of above about 26, i.e., an average of above about 26 carbon atoms per molecule. For example, the olefinic hydrocarbon mixture may have an average carbon number of above about 30 and contain alpha-olefinic hydrocarbons of from 28 to 35 carbon atoms, or have an average carbon number of above about 26 and contain alpha-olefin hydrocarbons of from 24 to 28 carbon atoms which is the most preferred alpha-olefin hydrocarbon mixture for use in the present invention.

Typically, the alpha-olefin hydrocarbon mixture which is chlorinated in accordance with the present invention consists mainly of normal alpha-olefins. The term "alpha-olefin" as used herein designates the presence of a double bond within the hydrocarbon molecule at a position intermediate a terminal carbon atom and the next adjacent carbon atom. These alpha-olefin hydrocarbon molecules are preferably monoolefinic in nature. The alpha-olefin hydrocarbon feed mixture is preferably substantially free of deleterious impurities, and may be selected from among those alpha-olefin mixtures derived from the production of synthetic detergents.

The preferred alpha-olefin hydrocarbon mixture as discussed above which is chlorinated in accordance with the present invention may optionally include a minor quantity of dissolved lower molecular weight olefinic hydrocarbons which contain less than about 20 carbon atoms per molecule (e.g., 16 to 18 carbon atoms per molecule) or a minor quantity of dissolved higher molecular weight olefinic hydrocarbons which contain an excess of about 35 carbon atoms per molecule (e.g., 40 to 50 carbon atoms per molecule).

An illustrative example of a most preferred alpha-olefin hydrocarbon mixture for use in the present invention is summarized below:

| Carbon number distribution, weight percent | |
| --- | --- |
| $C_{22}$ | Max. 3 |
| $C_{24}$ | 25 – 35 |
| $C_{26}$ | 40 – 50 |
| $C_{28}$ | 15 – 25 |
| $C_{30+}$ | 5 – 15 |
| Average carbon atoms per molecule | 26 – 28 |
| Specific gravity at 20° C | 0.815 (typical) |
| Saybolt color | +15 (typical) |
| Vicosity, secs., (SSU at 210° F) | 32 (typical) |
| Melting point, ° F (ASTM D-127) | 115 (typical) |

The chlorination reaction is typically conducted while the alpha-olefin hydrocarbon feedstock material is in the liquid state. During the reaction the alpha-olefin hydrocarbon material may be present as a melt, but is most preferably dissolved in an organic solvent for the same. Preferably the viscosity of the liquid during reaction is sufficiently low to permit substantially free evolution of hydrogen chloride so that the reaction progresses at a satisfactory rate.

In the most preferred embodiment the alpha-olefin hydrocarbon feedstock is dissolved in an organic solvent which is inert in the sense that it does not interfere with the desired reaction and which also serves as a diluent during the chlorination reaction. Preferred solvents are halogenated $C_1$ or $C_2$ hydrocarbons. For example, carbon tetrachloride, chloroform, pentachloroethane, perchloroethylene, 1,1,1-trichloroethane, 1,1,2-trichloroethane and ethylene dichloride may be used. The particularly preferred solvent is carbon tetrachloride. Any other solvent suitably inert under the reaction conditions may also be used as will be apparent to those skilled in the art. Typically, the alpha-olefin hydrocarbon feedstock is dissolved in a solvent in a concentration of from about 10% to about 50%, and preferably from about 20% to about 30%, by weight of the total solution.

The chlorination process of the present invention is preferably carried out in the presence of light to catalyze the reaction, although a catalyst may not be necessary in certain instances. Other catalysts such as Lewis acid catalysts, e.g., aluminum chloride and boron trifluoride, may also be used.

If desired, the use of a catalytic light source may be deferred until a significant degree of chlorination is achieved, e.g., until the product contains about 40% to about 50% chlorine.

Conventional actinic light sources commonly used in photochemical reactions may be selected from the following: fluorescent lamps, tungsten filament lamps, ordinary light bulbs, mercury vapor arc lamps such as a Hanovia light, and ultraviolet lamps. The light source may be placed directly inside the reactor, outside a transparent wall of the reactor, or next to an external recycling line through which the reactants circulate. Light wave lengths of below about 3000 angstrom units may produce harmful decomposition or an otherwise inferior product. Such wave lengths should be avoided and may be filtered out or eliminated as disclosed in U.S. Pat. Nos. 2,403,179 and 2,929,369, which are incorporated herein by reference.

The chlorination of alpha-olefin hydrocarbons according to the present invention may be conducted at any convenient temperature. For example, reaction temperatures may be from about 20° C to about 150° C, and more typically from about 35° C to about 100° C. When carbon tetrachloride is used as the solvent, reaction temperature between about 60° C and about 75° C, are preferably used.

The chlorination reaction is preferably carried out at substantially atmospheric pressure; however, slightly elevated pressures may be utilized and subatmospheric pressures may also be used if desired. The reaction may also be carried out on a batch, semicontinuous or continuous basis.

The chlorine is preferably introduced into the reaction zone as a gas. The rate of chlorine introduction is preferably adjusted so as to approximate the rate of reaction.

The liquid alpha-olefin solution undergoing chlorination is preferably stirred or otherwise agitated throughout the reaction, although a non-stirred reactor may be used if desired.

If desired, an additive capable of overcoming trace amounts of iron contamination optionally may be provided in the reaction zone in accordance with the teachings of commonly assigned U.S. Pat. No. 3,567,610 which is incorporated herein by reference.

As described therein, undesirable contaminations may be avoided during chlorination by chlorinating in the presence of a minor amount, e.g., from about 0.1 to about 1,000 ppm (parts per million) and preferably from 0.1 to 25 ppm of the alpha-olefin and any solvent, of an additive which is soluble in water or hydrochloric acid and selected from the group consisting of a ferrocyanide of a Group I or a Group II metal, a ferricyanide of a Group I or Group II metal, ammonium ferrocyanide, ammonium ferricyanide, ferrocyanic acid, ferricyanic acid, and preferably potassium ferrocyanide.

The chlorination reaction may be terminated by for example, ceasing chlorine introduction when the desired degree of chlorination has taken place. The progress of the chlorination reaction may be simply monitored by, for example, the periodic withdrawal of a sample followed by specific gravity determination. Chlorination is continued until a chlorinated alpha-olefinic hydrocarbon is formed having above about 65% chlorine, preferably between about 68% and about 70% chlorine.

Chlorination to levels above about 70% may introduce undesirable insoluble material into the resulting chlorinated alpha-olefin material. If such insoluble material is encountered at a chlorine content above about 70% for any specific alpha-olefinic feedstock, then that specific feedstock should be chlorinated to a slightly lower chlorine content to avoid the formation of such insolubles.

Chlorine content as used herein refers to the amount of chlorine chemically fixed or bonded to the alpha-olefin hydrocarbon molecules and not to any free chlorine or the chlorine content of any chlorinated solvent remaining in the chlorinated hydrocarbon material. Chlorine content can be conveniently measured by an oxygen bomb technique, e.g., ASTM procedure D 1638-70 which is incorporated herein by reference.

Conventional apparatus commonly utilized in chlorination of hydrocarbons may be selected for use in the present invention. Reactors are preferably glass-lined, and means are preferably also provided for refluxing during the chlorination reaction.

At the completion of the chlorination standard techniques may be employed to recover the chlorinated hydrocarbon of a relatively high degree of purity. For instance, air or other gas may be blown through the chlorinated product mixture to remove unreacted chlorine and any remaining hydrogen chloride by-product resulting from the chlorination reaction. Also, vacuum techniques may be utilized to improve the purity of the product.

Conventional soluble stabilizers may be blended with the chlorinated alpha-olefinic product to protect it from undue dehydrochlorination during storage and subsequent use particularly if elevated temperatures are encountered for extended periods of time. Generally, the addition of up to about 5% by weight of stabilizer is satisfactory. However, this amount may be adjusted depending upon the temperatures encountered and lengths of exposure to heat or light.

The resulting solid resinous chlorinated alpha-olefinic hydrocarbon material of the present invention typically contains above about 65% chlorine. Preferably, chlorine content is from about 68% up to about 70%. The chlorinated alpha-olefinic hydrocarbon material may also have a ring and ball softening point (ASTM E-28) above about 90° C, e.g., between about 90° and 120° C, more typically between about 90° and 95° C, and is completely soluble and gel-free initially and after 24 hours in aromatic hydrocarbon solvents such as xylene (50% colution −25° C.) The highly chlorinated alpha-olefinic hydrocarbon material of the present invention is also typically characterized by color (Gardner scale — 15 grams/100 ml carbon tetrachloride) of less than about 10, and more typically less than about 1.5; a specific gravity at 25° C of between about 1.58 and about 1.65, and more typically between about 1.60 and 1.63; a heat stability (JQD), %, under about 1, typically under about 0.5 and more typically between about 0.1 and about 0.3. The chlorinated alpha-olefinic hydrocarbon material of the present invention is also characterized by general non-toxicity and flame retardance and is soluble in a wide range of industrial solvents including chlorinated solvents, e.g., carbon tetrachloride; ethers, e.g., ethyl ether; ketones, e.g., methyl ethyl ketone; aromatic hydrocarbons, e.g., benzene, xylene and the like.

The present invention is further illustrated by the following examples; all parts, percentages and ratios in the following examples as well as in the specification and claims are by weight unless otherwise specified.

EXAMPLE I

Initially, 4,235 parts by weight of alpha-olefinic hydrocarbon material having the following specifications were charged to a glass-lined reaction vessel in molten form (70° C).

| | |
|---|---|
| Saybolt Color | +15 |
| Melt Point, °F | 115 |
| Specific Gravity (80° C), lb./gal | 7.75 |
| Viscosity (SSU, 210° F) secs., | 32 |
| Alpha-olefin Composition, % | |
| $C_{22}$ and lower | 0.8 |
| $C_{24}$ to $C_{28}$ | 86.8 |
| $C_{30}$ and higher | 12.4 |
| Average Carbon Number | 26.6 |

Next, 12,700 parts by weight of technical grade carbon tetrachloride were charged to the reaction vessel. With the aid of a propeller stirrer the alpha-olefin feed was completely dissolved within the carbon tetrachloride. The reaction vessel was provided with a Pyrex glass recycle line whereby a portion of the reactant could be continuously withdrawn from a lower portion of the reaction vessel and reintroduced at the top thereof. Situated next to the recycle line was a mercury vapor arc lamp.

Finely divided potassium ferrocyanide in a quantity of 0.3 parts by weight was dissolved in 2 parts by weight of water and added to the reaction vessel while agitation continued. Temperature of the reaction contents of the reaction vessel was 65° C. The light source was then actuated, the recycle begun and chlorine gas continuously introduced into the recycle line at a rate of 1,000 parts of chlorine per hour. When the degree of chlorination reached 50% by weight based upon the weight of the chlorinated product, the rate of chlorine introduction was reduced to 400 parts of chlorine per hour until a total of 16,000 parts by weight chlorine had been added to the reaction vessel. The carbon tetrachloride solvent was under reflux as the exothermic chlorination reaction progressed and the reactants were prevented from attaining a temperature in excess of about 70° C by refluxing the carbon tetrachloride in additional water cooling of the reaction vessel. After 20 hours the chlorinated alpha-olefin hydrocarbon contained approximately 70% by weight chlorine and the chlorination was terminated. Upon recovery, the chlorinated alpha-olefin was found to exhibit the following properties:

| | |
|---|---|
| Percent Chlorine | 69.0 |
| Color (Gardner — 15 gms/100 ml $CCl_4$) | <1 |

| | |
|---|---|
| Ring and Ball, ° C | 92 |
| Specific Gravity (25° C) | 1.61 |
| Heat Stability (JQD) | 0.16% |

A 50% solution of the resulting chlorinated alpha-olefin product in xylene was completely soluble and gel free initially and after 24 hours at 25° C.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the present invention.

We claim:

1. A solid resinous chlorinated alpha-olefinic hydrocarbon material, which chlorinated alpha-olefinic hydrocarbon material contains above about 65% chlorine; has a ring and ball softening point of above about 90° C; and is completely soluble and gel-free initially and after 24 hours in xylene (50% solution −25° C.)

2. A solution of an aromatic hydrocarbon solvent in which the alpha-olefinic hydrocarbon of claim 1 is completely dissolved.

3. A solid resinous chlorinated alpha-olefinic hydrocarbon material according to claim 1, wherein the chlorinated alpha-olefinic hydrocarbon material consists essentially of a mixture of chlorinated alpha-olefinic hydrocarbons containing on the average above about 26 carbon atoms per molecule and selected from the group consisting of alpha-olefinic hydrocarbons having from about 20 carbon atoms to about 35 carbon atoms.

4. A solid resinous chlorinated alpha-olefinic hydrocarbon material according to claim 3, wherein the mixture of chlorinated alpha-olefinic hydrocarbons consists essentially of a mixture of $C_{24}$ to $C_{28}$ chlorinated alpha-olefin hydrocarbons.

5. A solid resinous chlorinated alpha-olefinic hydrocarbon material according to claim 3, wherein the chlorinated alpha-olefinic hydrocarbon material consists essentially of a mixture of $C_{28}$ to $C_{35}$ chlorinated alpha-olefin hydrocarbons.

6. A solid resinous chlorinated hydrocarbon material having improved solubility in aromatic solvents, which chlorinated hydrocarbon material contains above about 65% chlorine; has a ring and ball softening point of above about 90° C; is completely soluble and gel-free initially and after 24 hours in xylene (50% solution −25° C;) and consists essentially of a mixture of $C_{24}$ to $C_{28}$ chlorinated alpha-olefinic hydrocarbons.

7. A solution of an aromatic hydrocarbon solvent in which the alpha-olefinic hydrocarbon of claim 6 is completely dissolved.

8. A solid resinous chlorinated alpha-olefinic hydrocarbon material according to claim 6, wherein the chlorinated alpha-olefinic hydrocarbon material has a color (Gardner scale — 15 grams/100 ml CCl$_4$) of less than about 10 and a specific gravity at 25° C of between about 1.58 and 1.65.

9. A solid resinous chlorinated alpha-olefinic hydrocarbon material consisting essentially of a mixture of $C_{24}$ to $C_{28}$ chlorinated alpha-olefin hydrocarbons and having an average carbon number of above about 26; and having a chlorine content of between about 68% and about 70%; a ring and ball softening point of between about 90° C and about 95° C; a color (Gardner scale — 15 grams/100 ml CCl$_4$) of less than about 1.5; a heat stability (JQD) between about 0.1% and about 0.3%; a specific gravity at 25° C of between about 1.60 and 1.63 and being completely soluble and gel-free initially and after 24 hours in xylene (50% solution −25° C.)

10. A solution of an aromatic hydrocarbon solvent in which the alpha-olefinic hydrocarbon of claim 9 is completely dissolved.

11. A process for producing a highly soluble, solid, resinous, highly chlorinated hydrocarbon material, which process comprises chlorinating in the presence of a catalytic amount of light an alpha-olefinic hydrocarbon feed, dissolved in an inert organic solvent during chlorination, until a highly chlorinated alpha-olefinic hydrocarbon material is produced, which alpha-olefinic hydrocarbon material contains above about 65% chlorine; has a ring and ball softening point of above about 90° C; and is completely soluble and gel-free and after 24 hours in xylene (50% solution−25° C.)

12. A process for production of a highly soluble solid resinous highly chlorinated hydrocarbon material, which process comprises chlorinating an alpha-olefin hydrocarbon feed consisting essentially of a mixture of chlorinated alpha-olefinic hydrocarbons having an average carbon number of above about 26 and selected from the group consisting of alpha-olefinic hydrocarbons of from about 20 carbon atoms to about 35 carbon atoms at a temperature of between about 20° C and about 150° C and in the presence of a catalytic amount of light and a minor amount of an additive which is soluble in water or hydrochloric acid and is selected from the group consisting of ferrocyanides of Group I and Group II metals, ferricyanides of Group I and Group II metals, ammonium ferrocyanide, ammonium ferricyanide, ferrocyanic acid and ferricyanic acid to produce a chlorinated alpha-olefinic hydrocarbon material containing above about 65% chlorine; having a ring and ball softening point of above about 90° C, and being completely soluble and gel-free initially and after 24 hours in xylene (a 50% solution −25° C.)

13. A process according to claim 12 which further comprises dissolving the highly chlorinated alpha-olefinic hydrocarbon material in a solvent.

14. A process according to claim 12, wherein the alpha-olefinic feed consists essentially of a mixture of alpha-olefinic hydrocarbons selected from the group consisting of alpha-olefinic hydrocarbons having from about 24 to about 28 carbon atoms and the mixture having an average carbon number of above about 26.

15. A process according to claim 12 wherein the highly chlorinated alpha-olefinic hydrocarbon material that is produced has a color (Gardner scale — 15 grams100/ ml CCl$_4$) of less than about 10 and a specific gravity at 25° C of between about 1.58 and 1.65.

16. A process according to claim 12 wherein the alpha-olefinic hydrocarbon feed is dissolved in an inert organic solvent during chlorination.

17. A process for producing a solid resinous chlorinated alpha-olefinic hydrocarbon material, which process comprises chlorinating at a temperature of between about 50° C and about 100° C a liquid reaction mixture of an alpha-olefin hydrocarbon feed consisting essentially of a mixture of alpha-olefinic hydrocarbons having an average carbon number of above about 26 and selected from the group consisting of alpha-olefinic hydrocarbons of from 24 to 28 carbon atoms and dissoved in inert organic solvent and in the presence of a catalytic amount of light and in the presence of from about 0.1 to about 25 ppm intimately dispersed potassium ferrocyanide to produce a solid resinous chlorinated alpah-olefinic hydrocarbon material having a chlorine content of between about 68% and about 70%; a ring and ball softening point of between about 90° C and about 95° C; a color (Gardner scale — 15 grams/100 ml $CCl_4$) of less than about 1.5; a heat stability (JQD) of between about 0.1 and about 0.3; specific gravity at 25° C of between about 1.60 and 1.63 and being completely soluble and gel-free initially and after 24 hours in xylene (50% solution −25° C.)

18. A process according to claim 17, which process further comprises dissolving the solid resinous chlorinated alpha-olefinic hydrocarbon in a solvent.

19. A process according to claim 17 wherein the liquid reaction mixture contains between about 10% and about 50% alpha-olefin and the organic solvent is carbon tetrachloride.

* * * * *